(12) United States Patent
de Penning et al.

(10) Patent No.: US 11,517,757 B2
(45) Date of Patent: Dec. 6, 2022

(54) NON-THERMA PLASMA DEVICE WITH ELECTROMAGNETIC COMPATIBILITY CONTROL

(71) Applicant: PlasmaCure B.V., Nijmegen (NL)

(72) Inventors: Johannes Pieter de Penning, Eindhoven (NL); Paulien Smits, Eindhoven (NL); Wouter Bastiaan Zeper, Eindhoven (NL)

(73) Assignee: PlasmaCure B.V., Nijmegen (NL)

( * ) Notice: Subject to any disclaimer, the term of this patent is extended or adjusted under 35 U.S.C. 154(b) by 870 days.

(21) Appl. No.: 16/348,397

(22) PCT Filed: Nov. 17, 2017

(86) PCT No.: PCT/NL2017/050748
§ 371 (c)(1),
(2) Date: May 8, 2019

(87) PCT Pub. No.: WO2018/093261
PCT Pub. Date: May 24, 2018

(65) Prior Publication Data
US 2020/0069956 A1 Mar. 5, 2020

(30) Foreign Application Priority Data
Nov. 18, 2016 (NL) ..................... 2017822

(51) Int. Cl.
*A61N 1/04* (2006.01)
*A61N 1/44* (2006.01)
*H05H 1/24* (2006.01)

(52) U.S. Cl.
CPC ............. *A61N 1/44* (2013.01); *A61N 1/0492* (2013.01); *H05H 1/2406* (2013.01); *A61N 1/0468* (2013.01); *A61N 1/0484* (2013.01)

(58) Field of Classification Search
CPC ...... A61N 1/44; A61N 1/0492; A61N 1/0468; A61N 1/0484; A61N 1/326; A61N 1/327;
(Continued)

(56) References Cited

U.S. PATENT DOCUMENTS

| 5,181,423 A * | 1/1993 | Philipps .................. G01L 9/125 |
| | | 702/140 |
| 9,005,188 B2 * | 4/2015 | Wandke ............... A61N 1/0408 |
| | | 606/32 |

(Continued)

FOREIGN PATENT DOCUMENTS

| DE | 102014220488 A1 | 4/2016 |
| KR | 101407672 B1 | 6/2014 |

OTHER PUBLICATIONS

European Patent Office, International Search Report in corresponding International Application No. PCT/NL2017/050748, dated Apr. 3, 2018 (3 pages).
(Continued)

*Primary Examiner* — Carl H Layno
*Assistant Examiner* — Anh-Khoa N Dinh
(74) *Attorney, Agent, or Firm* — Leydig, Voit & Mayer, Ltd.

(57) ABSTRACT

An electrode arrangement is described that is configured to be coupled to a high voltage source for a dielectric barrier discharge plasma treatment of an irregularly three-dimensionally shaped surface of an electrically conducting body. The three-dimensionally shaped surface is used as a counter electrode. A first planar electrode is coupled to the high voltage source via a first lead, fitted to the object to be treated and brought in contact with a dielectric. A second electrode is contacted with the surface to be treated as reference electrode. The second electrode is provided in an edge portion that is circumferential to the first planar electrode and configured to be coupled to a reference voltage
(Continued)

source via a second lead. An isolating cover layer covers the electrode and a third electrode covers the isolating cover layer as a ground electrode.

11 Claims, 8 Drawing Sheets

(58) Field of Classification Search
CPC ............... H05H 1/2406; A61B 18/042; A61B 2018/0047; A61B 2018/122
See application file for complete search history.

(56) References Cited

U.S. PATENT DOCUMENTS

| | | | |
|---|---|---|---|
| 2006/0003482 A1* | 1/2006 | Chinthakindi | H01G 5/38 438/52 |
| 2014/0182879 A1 | 7/2014 | Busse et al. | |
| 2015/0343231 A1 | 12/2015 | Sanders et al. | |
| 2015/0371829 A1 | 12/2015 | Koyama et al. | |
| 2016/0236002 A1 | 8/2016 | Dirk et al. | |
| 2016/0331989 A1 | 11/2016 | Cho et al. | |
| 2019/0223280 A1* | 7/2019 | Wandke | A61N 1/44 |

OTHER PUBLICATIONS

Ayan et al., "Application of Nanosecond-Pulsed Dielectric Barrier Discharge for Biomedical Treatment of Topographically Non-Uniform Surfaces," Journal of Physics D: Applied Physics, Institute of Physics Publishing Ltd, GB, vol. 42, No. 12, pp. 1-5, XP020158376 (Jun. 21, 2009).

* cited by examiner

1

11

111

NON-THERMA PLASMA DEVICE WITH ELECTROMAGNETIC COMPATIBILITY CONTROL

CROSS-REFERENCE TO RELATED APPLICATIONS

This patent application is a U.S. National Phase of PCT International Application No. PCT/NL2017/050748, filed Nov. 17, 2017, which claims priority to Netherlands Application No, 2017822, filed Nov. 18, 2016, which are both expressly incorporated by reference in their entireties, including any references contained therein.

FIELD OF THE INVENTION

This invention relates to devices for generating non-thermal plasma, which can treat a large area. In particular, the invention relates to devices that can be applied e.g. for preventing diabetic foot complications.

BACKGROUND OF THE INVENTION

Cold plasmas have considerable potential for skin conditioning, disinfection of skin and wound healing. However, available plasma sources lack the possibility to treat larger areas, to control plasma properties and/or the possibility to adapt the shape of the plasma to the shape of the object to be treated (e.g. a foot). This invention focuses on: a cold plasma device, which can treat a larger area.

- Cold plasmas allow efficient, contact-free and painless disinfection, even in microscopic openings, without damaging healthy tissue.
- The bacterial response to plasma application is almost instantaneous (few seconds).
- The plasma is directly in contact with the skin which may result in fast disinfection of the skin.
- When operated in air a high production of NO radicals may be expected. The production of NO might have a positive effect on the microcirculation of blood in the skin, which is very important in the case of diabetic foot.
- A considerable, transient electric field will be present in/near the skin (several kV/cm). Such electrical fields result in faster proliferation of skin cells. Also a positive effect on blood circulation might occur due to electroporation of skin.
- Provides a microbial defense system for plasma application (and hence resistance build-up).
- Plasmas can stimulate human cells without damage. Clinical trials confirm the efficacy and tolerability of plasma in treating infected chronic wounds.
- Plasmas could contribute to a better skin condition and a higher ability for wound healing due to an improved microcirculation.
- Plasma device according to this invention support preventing serious foot complications at an early stage, and contributes to skin improvement, wound prevention and healing.
- Nowadays, the only preventive actions that people with diabetes mellitus can take at home, is daily inspection and daily cleaning of the feet. However, this is often not practical for high-risk patients due to poor eyesight, obesity and stiff joints. World-wide there are no home-care devices available.
- The invention provides an easy to use, fool-proof home-care device that solves this problem.
- Because of the costs involved it is crucial that patients treat their feet every day. However, patients with diabetic foot complications are relatively old and tend to forget.
- The flexible plasma device is a platform technology with a number of interesting applications and market possibilities to improve skin conditions, prevent ulcerations and accelerate healing of the diabetic foot.
- The plasma can easily be delivered to the skin of a patient, e.g. in the form of a plasma pad. The skin will be temporary exposed to the plasma to disinfect the skin and to improve cell proliferation and microcirculation of the blood. Typically, one-minute plasma treatment will reduce the bacterial load on the foot with up to a factor of one million, without negatively affecting the skin. Such a treatment should be continued on a once/twice per day basis until the threat of infection has been overcome.

This technology offers perspectives for medical treatments and prevention measures. In dermatology, new opportunities are being opened for wound healing, tissue regeneration, therapy of skin infections, and probably many more applications. Also, plasmas may effectively kill skin-cancer cells. A few examples:

- Skin diseases: Most dermatological problems are associated with bacterial or fungal infections. Plasmas may help to reduce complications due to bacteria and fungi, and may even treat the diseases themselves.
- Chronic wounds and inflammations: Plasmas may very well assist in controlling the consequences of chronic inflammation associated with these diseases by eliminating bacterial and fungal infections, which results in a drastic improvement of the quality of life.
- Hospital hygiene: The growth of resistant bacteria (e.g. MRSA) poses a big problem in hospitals. Plasma devices can sterilize or disinfect both medical tools and hands (e.g. of surgeons).
- Antifungal treatment: It has been shown that plasmas can be employed efficiently to combat fungal diseases.

From U.S. Pat. No. 9,005,188 and EP2670477 flexible electrodes are known with a structured surface of a plurality of spaced apart projections from the surface to form air-guiding areas where the plasma is generated. A problem associated with these devices is the high voltage oscillations, that is caused by irregular discharges of the plasma. This poses problems for electromagnetic compatibility. The switching flyback transformer and the combination with plasma on an open pad can produce a lot of interference. The plasma pad itself is the biggest source of radiation because high voltage is applied to an open mesh that will act as a radio antenna emitting electromagnetic radiation. Furthermore, the large non differential wires, acting as a loop antenna, cause a radiating surface. Some publications mention a shielding cover as method to prevent high electromagnetic radiation when using a volume dielectric barrier discharge (DBD). However, none of these solutions are satisfying for a device that is to be used in home and medical care environments.

SUMMARY OF THE INVENTION

In summary, embodiments of the invention pertain to: an electrode arrangement to be coupled to a high voltage source for a dielectric barrier discharge plasma treatment of an irregularly three-dimensionally shaped surface of an electrically conducting body, which surface is used as a counter electrode, having a first electrode to be coupled to the high voltage source via a first lead;
a dielectric which is formed by a flexible material in such a way that the dielectric shields the first planar electrode from the surface to be treated;
a spacer defining a structured surface on a side of said arrangement facing a surface to be treated,
said first electrode being fitted to the object to be treated and brought in contact with the dielectric,
a second electrode that is to be contacted with the surface to be treated as reference electrode, said second electrode provided in an edge portion being circumferential to the first electrode and to be coupled to a reference voltage source via a second lead,
an isolating cover layer covering the electrode and
a third electrode covering said isolating cover layer as a ground electrode.

Accordingly the reference electrode provides current paths that are differential in design. In particular, for the first electrode, the discharge currents will follow a racial path, thereby cancelling electric field strengths and reducing electromagnetic radiation. Additionally to that, a grounded shielding cover electrode is provided over the pad. In another aspect, the second electrode of the electrode arrangement has a pairing portion that extends from a ring portion to match the first lead. This further adds to the differential design, in that it reduces the electromagnetic generated by the first lead.

DETAILED DESCRIPTION

Figure 1:
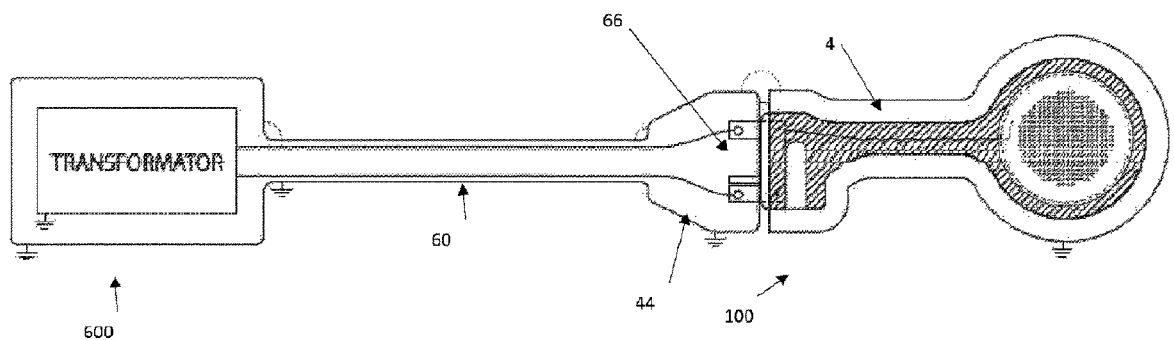
FIG. 1 shows a schematic perspective view of a system configuration of the cold plasma device.

FIG. 1 shows a schematic perspective view of a prototype of the cold plasma device. The plasma device 100 provides a dielectric barrier discharge (DBD) technique for plasma generation. The DBD concept will be briefly explained here with reference to FIG. 3. The plasma can be powered by repetitive, short high-voltage pulses (ns-µs duration, up to a few 100 kHz repetition rate). For example, a driver circuit 600 is provided for driving the planar electrode, wherein the driver circuit drives the planar electrode in a pulsed voltage in a range of 3-8 kV, in a range of 0.5-100 kHz, and a pulse duration in a range of 1 nano to 150 micro second. This allows for a pulse rate that substantially provides a micro discharge wherein electrical current through the object to be treated (skin, human body) will only flow during the time that the plasma is on (which is typically equal to the HV pulse duration). In between the pulses, the plasma is not active, and no current flows through the skin.

The pulsed operation of the plasma enables perfect control over the power of the plasma by means of the pulse repetition rate. In this way, the plasma power can be controlled and adjusted without affecting the plasma properties.

Due to the pulsed operation, treatments can be performed at adjustable and controllable pulse sequences, duty cycles and bursts of pulses with varying duration. Pulse sequences can be optimized towards a specific application. To achieve a good electromagnetic compatibly for the complete system 600 a protective earth shielding 44 is needed to screen off the cable 60, reducing the radiation from the cable. The shielding 44 will be attached to the grounded casing of the source 600. The same grounded shielding 44 of the casing will be connected, via a connector 66 to the shielding 4 of the plasma device 100 and will thereby completely screen of the treatment area (See FIG. 7). Some ferrite cores on the output of the source may filter the frequencies induced by the HV transformer on the cable, and reduces the radiation of the common mode. Also the shielding of the HV Transformer should be such that it reduces the outgoing radiation and reduce the internal interference on the power electronics.

Figure 2:
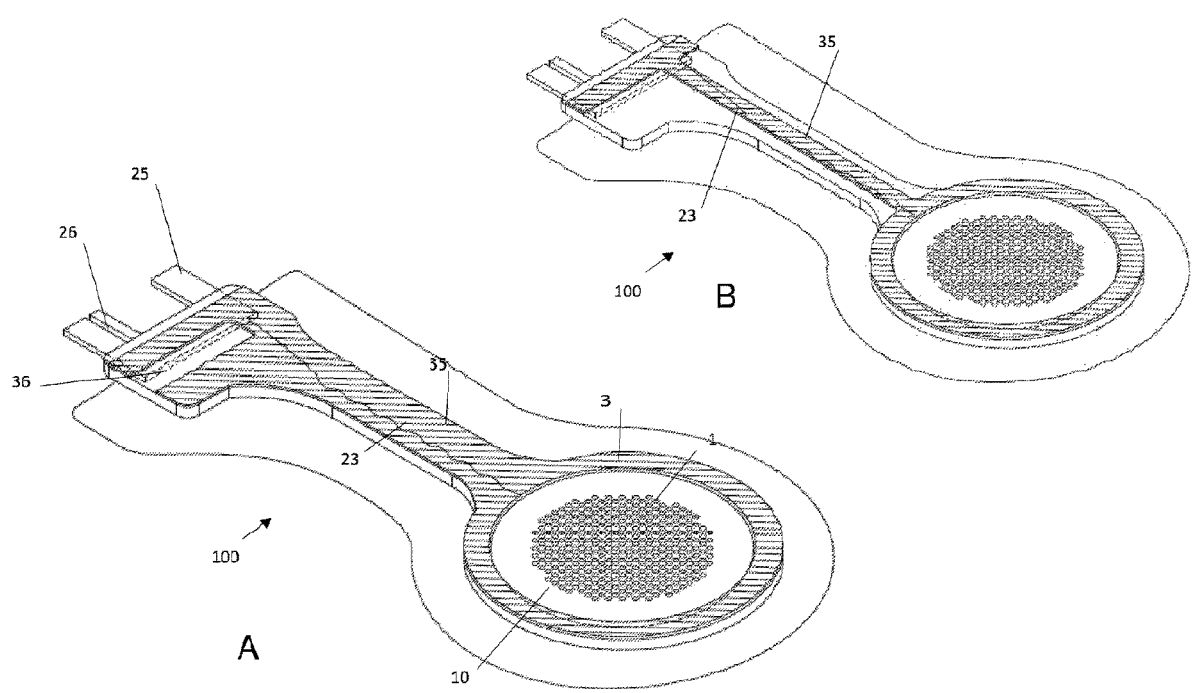
FIGS. 2A and B show the device of FIG. 1 in schematic cross sectional view.
Figure 3A:
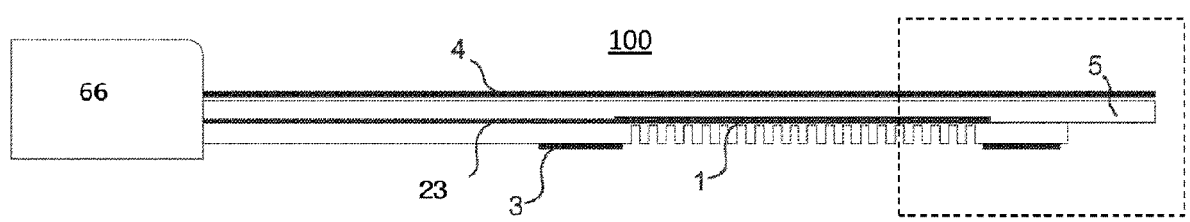
FIGS. 3A and B show edge details of the cross sectional view in FIGS. 2A and B.
Figure 3B:
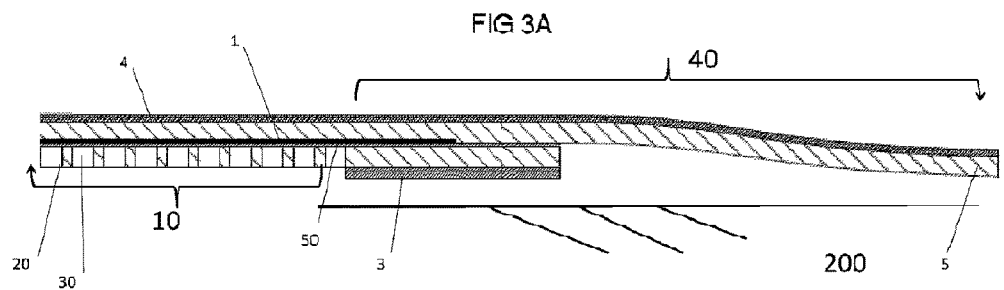

FIG. 2A shows that the plasma device 100 comprises a planar electrode 1 covered with a dielectric foil or film (see FIG. 3). A gas (or air) gap is present in a treatment area 10 formed between an object to be treated (e.g. foot) being functioning as electrode 1 and dielectric with a dielectric constant e.g. larger than 2. The treatment area is bounded by reference electrode 3. In contrast to an electrode 1 made from metal foil, a mesh is suitably adaptable to the 3D shape, and will not rupture, crease or fold. The mesh may be contacted by a lead 23, that connects to a high voltage clamp 25, and a reference electrode clamp 26 that connects to the second reference electrode 3 respectively, said lead 23 paired with a portion 35. The pairing portion 35 extends to a high voltage clamp with a cut-out portion 36 extending between the high voltage clamp 25 and a reference electrode clamp 26. This cut-out forces the return current to pair with the high voltage lead 23. Reference voltage electrode 3 is provided in an edge portion being circumferential to the first electrode 1. The ring shaped electrode 3 is in contact with the skin to be treated, and is circumferential to the treatment area. It may be provided with a sticky conductive layer to enhance the conductive properties to the object to be treated, which optimizes the electric coupling with the skin and prevents plasma to escape. Other circumferential designs may include electrode forms that follow a contour of the inner electrode 1 along a circumference, e.g. an electrode that partly surrounds the planar electrode. The circumferential electrode may also be one or more separate electrodes placed near the plasma electrode 1 and following its circumference. FIG. 2B shows a similar design of the device 100, but now with a pairing portion that only pairs with lead portion, and connects to the clamp 26, without a cut out FIGS. 3A and 3B show in more detail a side view of the plasma device 100 coupled to high voltage source 600. For ease of understanding in FIG. 3B, object to be treated 200 is shown apart from device 100, but in use, edge 44 and electrode 3 firmly contact object 200. The electrode 1 is powered by pulsed high-voltage. Due to the dielectric 50, the electric field is mainly present in treatment area 10 formed between spacer structure or protrusions 20 in the structured surface 30. The protrusions 20 ensure a minimum distance of the electrode 20 to the object 200 e.g. larger than 1 mm. If the electric field is high enough (>30 kV/cm) and if the thickness of the air gap is rather constant, homogeneous cold plasma is created in the air gap to the object to be treated (e.g. the skin of a foot). Dielectric and protrusions have a high dielectric strength, e.g. >180 kV/mm.

A DBD cold plasma device can treat large areas; the dimensions of the DBD can be chosen over wide margins. Instead of allowing for airflow between the cold plasma device and the skin, discrete compartments 30 may be formed that will contain some air, but these need not be connected to each other. They may be isolated from each other, and may also be isolated to the surroundings by a closed edge.

The advantage is that the reactive gases that we will generate during operation of the cold plasma, gases like ozone cannot escape. This has the advantage that the device is more efficient: all reactive specimens are available to kill pathogens, and that the release of any toxic gases like ozone will be minimized.

Accordingly an electrode arrangement 100 is shown for a dielectric barrier discharge plasma treatment of an irregularly three-dimensionally shaped surface of an electrically conducting body. The body is typically a human body part, such as a foot, heel, toe, finger or any other diseased skin part, which surface is used as a counter electrode.

The arrangement has a first planar electrode 1 to be coupled to a high voltage source; a dielectric 50 (see FIG. 3B) which is formed by a flexible material in such a way that the dielectric 50 shields the first planar electrode from the surface to be treated; a spacer structure 20 defining a structured surface on a side of said arrangement 100 facing a surface 200 to be treated, such that the structured surface forms one or more spaced compartments 30 that are isolated by an ring shaped electrode 3 from the surroundings in order to prevent airflow between the surroundings and the compartments 30. Furthermore, it can be seen that the structured surface comprises an edge portion 40 wherein the grounded shield electrode 4 extends into the edge portion 40. By extending the planar electrode 1 above ring shaped reference electrode 3, separated by a suitable isolator, a solution may be provided for a problem of preventing break through near the edge portion of the electrode 1.

The device 100 has an electrode 1 that is fitted to the object to be treated 200 and brought in contact with the dielectric, in order to provide a substantially conformal compartment that follows the contours of the 3D shaped body for providing a homogenous microdischarged plasma. By an electrode 1 fitted to the object to be treated, the occurrence of saddle points or sharp folds prevents undesired local field strengths. It may be desirable to shape the electrode centrally to a concave or convex form of the surface to be treated, to optimize the local stretch of the electrode 1, so that the device optimally adapts to the object 200.

Figure 4:
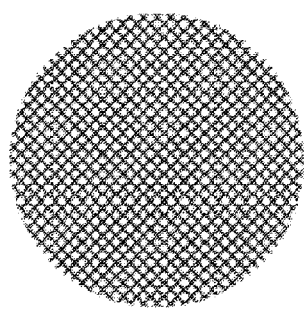
FIG. 4 show various embodiments of the planar electrode of the cold plasma device of the previous Figures.
Figure 4:
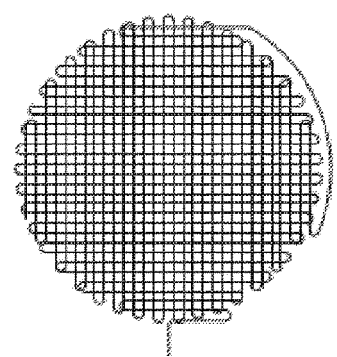
Figure 4:
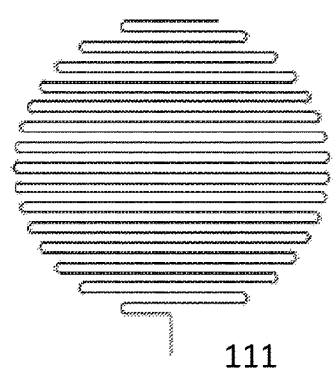

FIG. 4 shows a variety of embodiments for the first high voltage electrode 1, 11, 111. A particularly suitable embodiment is provided wherein the first planar electrode is a mesh. It is shown that the mesh may be provided by woven conductive threads, typically metallic, with a weave that allows in plane deformations. In contrast to electrode 1, that has a weave with straight non-connected parallel wires, electrode structure 111 by forming the first electrode from a continuous conductive wire. In this embodiment, a weave from a single wire, or from wires with a non-intersecting meandering pattern, further prevents breakthrough problems. In another electrode weave 11, the wire is provided with intersecting meandering weave pattern. It was found that a mesh is stretchably deformable around three dimensional of an object to be treated, such as a heel, finger or toe, while still being able to provide a suitable homogenous plasma. It will be understood that 'stretchable' is to be understood in a conventional context known to the skilled person, i.e. in contrast to merely being flexible but non deformable in a planar length dimension, able to deform in a planar dimension typically more than 2-5% or even 10% of a length dimension.

Figure 5:
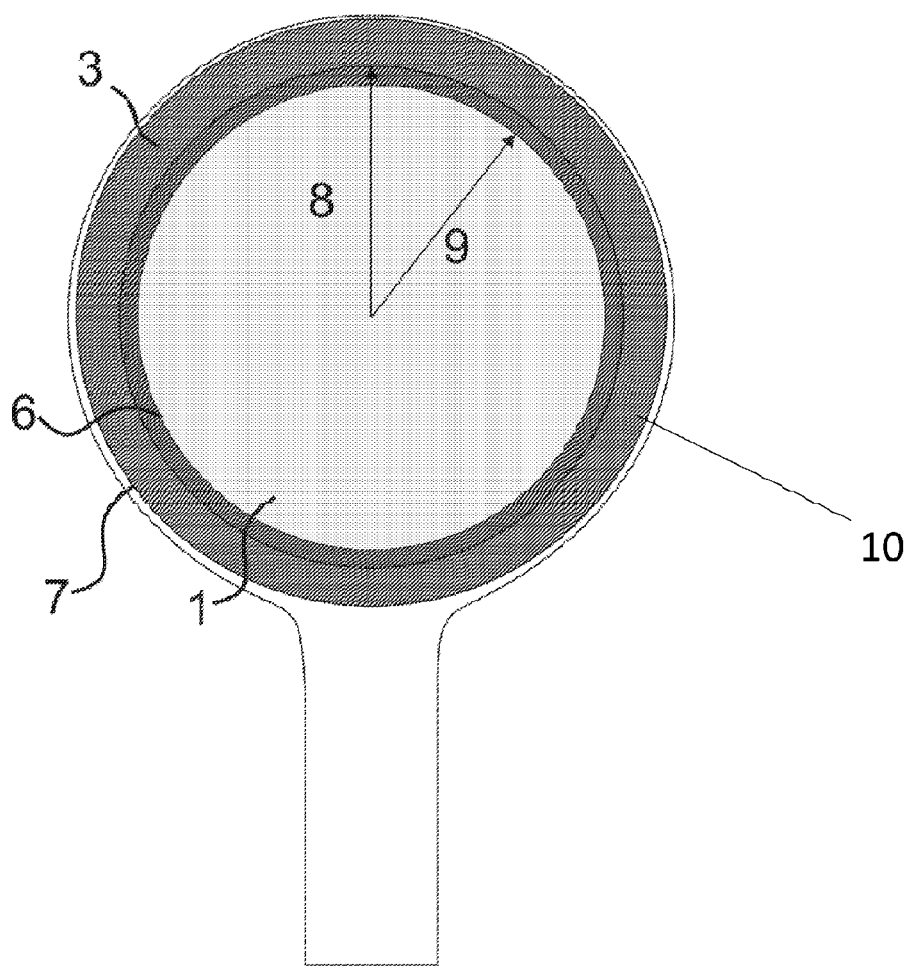
FIG. 5 in more detail concerns the reference electrode.

FIG. 5 in more detail concerns the reference electrode 3 (second electrode) that is to be contacted with the surface to be treated. The shape of the electrode 1 (high voltage electrode) and the inner side 6 of the reference electrode 3 are preferably round to give the design the best differential performance. A round shape has an unlimited number of symmetrical axes and the more symmetrical axes the shape has, the better the differential design is. The outside shape 7 of the reference electrode may be any shape—see also FIG. 6, and will therefore be the shape of the pad itself. The radius 8 of the electrode 1 is preferably bigger than the radius 9 of the inner side of the reference electrode 3. This makes centering of the electrode 1 inside the reference electrode 3 easier. A good centered electrode 1 is advantageous to ensure a good differential design.

Figure 6:
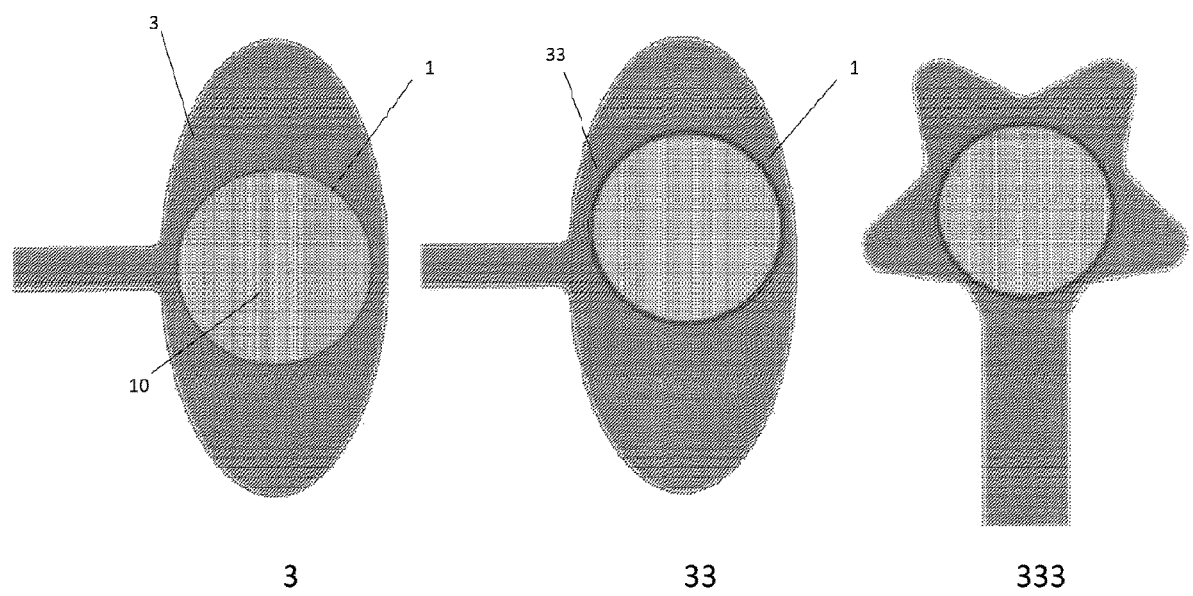
FIG. 6 shows a variety of reference electrode structures.

FIG. 6 shows a variety of reference electrode structures 3, 33 and 333. A difference between electrode structure 3 and 33 is that in 3, electrode 1 fully covers the plasma area. In that case the shape of this electrode 1 may be round but can also be variable, whereas the ideal shape for the plasma area 10 is a round shape.

If the electrode 1 is smaller than the treatment area 10, the ideal shape of the electrode 1 is a round shape, and should be centered in the plasma area 10 of the patch.

Figure 7:
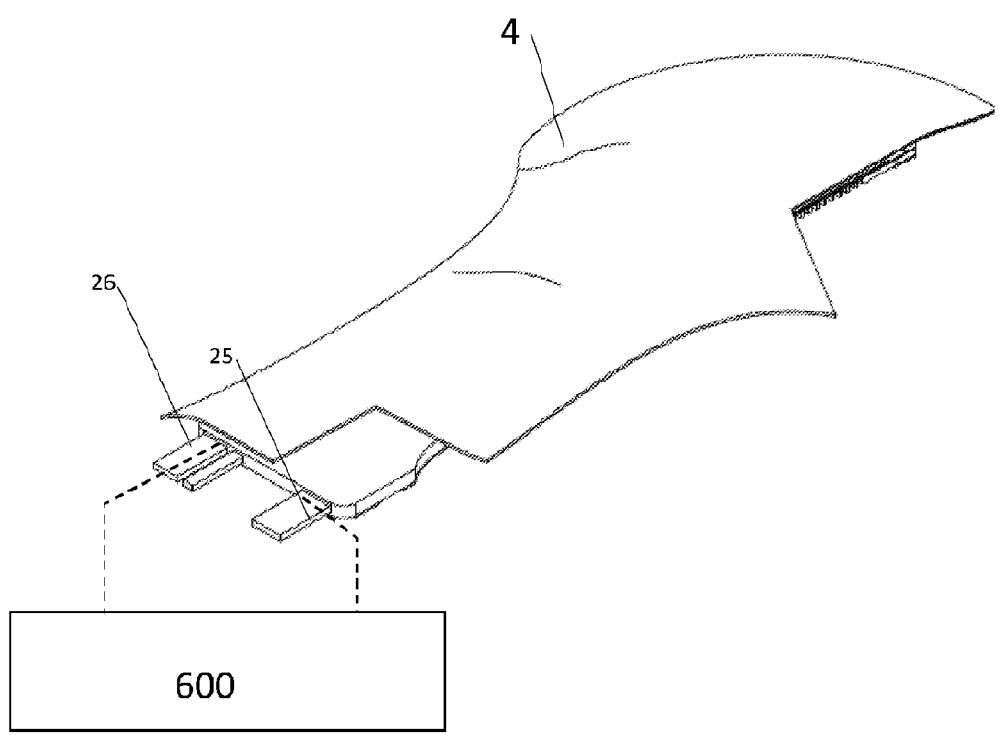
FIG. 7 shows a planar conductive shield.

More specifically, FIG. 7 shows that a third planar shielding electrode 4 completely covers said stretchable isolating cover layer 5. The planar electrode 4 is connected to ground potential and may or may not be in contact with the patient in use. The second (reference) electrode is floating relative to ground electrode 4 preventing currents running via the patient outside the wound area In use the patient may or may not be grounded.

Figure 8:
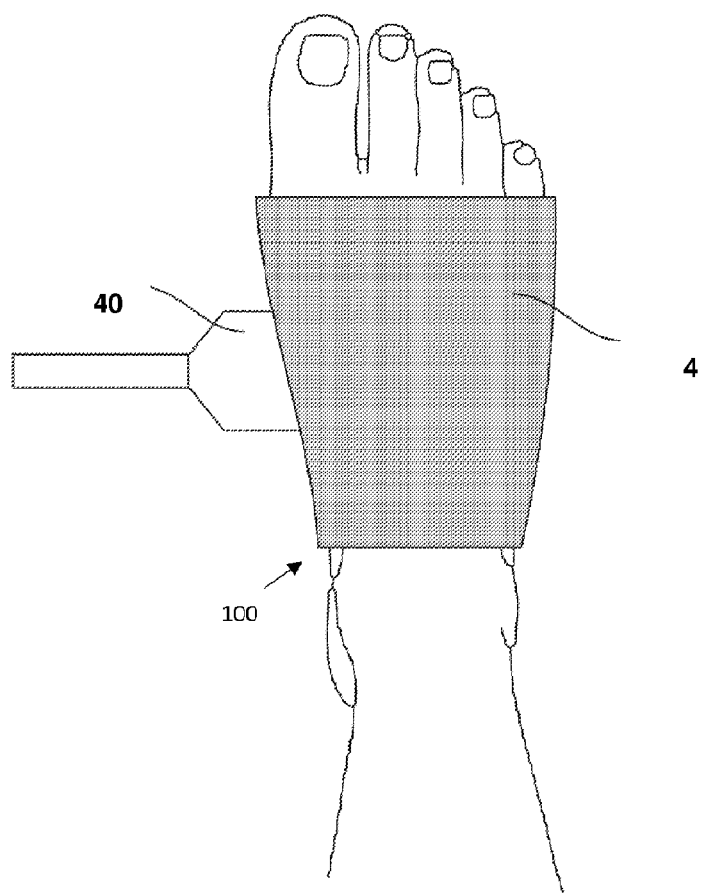
FIG. 8 shows a practical illustration of the plasma treatment device.

FIG. 8 shows a practical illustration of the plasma treatment device 100 with grounded electrode 4 completely covering the plasma treatment area of a foot to be treated. The grounded electrode is conductively coupled to shielded cable 60. In order to give a complete shielding to the system, the open side towards the treatment area needs to be covered too, beside of the connector 40. This is done by further extending a shielding electrode 4 around the body parts of the patient.

Further Embodiments

The driver circuit may comprise a planar electrode identification circuit. The connector has a sense (or identification) contact (not shown), so that the driving unit can detect:
what kind of cold plasma device is connected and adjust its power settings
if a cold plasma device is connected at all, for safety purposes
if a cold plasma device is correctly connected, for safety purposes
This can for example be realized by integrating a matching impedance or impedance circuit to the connector so that the impedance is matched to identify the connector.
The plasma device can be used at various levels in the medical care system: by the patient himself (e.g. as a homecare device), in primary health care (e.g. by a podiatrist or family doctor), in an outpatient clinic, or in a medical centre or hospital.

Variations to such embodiments, one could have the following additions or changes:

When the high voltage (HV) connection comes from the side which has the advantage of maximum flexibility, and makes it easier to make the device "see through".

When the HV connection comes from the rear, has the advantage that the device will be more compact The electrode arrangement is substantially transparent, so that an underlying body and the created plasma can be visually inspected. Specifically the dielectric material and the electrode are transparent so that it is possible to see the plasma in operation and to see the area under the plasma device (the wound). More specifically the isolating cover layer and spacer are provided from a single transparent flexible preform.

The invention claimed is:

1. An electrode arrangement to be coupled to a high voltage source for a dielectric barrier discharge plasma treatment of an irregularly three-dimensionally shaped surface to be treated, of an electrically conducting body, that is used as a counter electrode, the electrode arrangement comprising:
    a first planar electrode to be coupled to the high voltage source via a first lead;
    a dielectric formed by a flexible material in such a way that the dielectric shields the first planar electrode from the surface to be treated; and
    a spacer defining a structured surface on a side of the electrode arrangement facing the surface to be treated,
    wherein, during the dielectric barrier discharge plasma treatment, said first planar electrode is constructed to be fitted to an object to be treated and contacts the dielectric, and
    wherein the electrode arrangement further comprises:
        a second electrode that, during the dielectric barrier discharge plasma treatment, is configured to be contacted with the surface to be treated and functions as a reference electrode wherein the second electrode is provided in an edge portion that is circumferential to the first planar electrode and is coupled to a reference voltage source via a second lead;
        an isolating cover layer covering the first planar electrode; and
        a third electrode covering said isolating cover layer as a ground electrode.

2. The electrode arrangement, according to claim 1, wherein the first lead connects to a high voltage clamp, and the second lead connects to a reference voltage clamp.

3. The electrode arrangement, according to claim 1, wherein the second lead has a pairing portion that extends from the edge portion to pair the first lead.

4. The electrode arrangement, according to claim 3, wherein the pairing portion extends to a high voltage clamp with a cut-out portion extending between the high voltage clamp and a reference electrode clamp.

5. The electrode arrangement, according to claim 1, wherein the second electrode comprises a conductive sticker edge.

6. The electrode arrangement, according to claim 1, wherein the first planar electrode is a stretchable mesh.

7. The electrode arrangement, according to claim 1, wherein the first planar electrode is formed from a continuous conductive wire.

8. The electrode arrangement, according to claim 1, wherein the first planar electrode is formed from a conductive wire that is coated with a dielectric.

9. The electrode arrangement, according to claim 1, wherein the first planar electrode is connected to a contact with slide contacts of a printed circuit board (PCB) connector.

10. The electrode arrangement, according to claim 1, further comprising a driver circuit for driving the first planar electrode that is coupled to the high voltage source, wherein the driver circuit drives the first planar electrode in a pulsed voltage in a range of 3-8 kV, repetition rate in a range of 0.5-100 kHz, and a pulse duration in a range of one nanosecond to 150 microseconds.

11. The electrode arrangement according to claim 10 wherein the driver circuit comprises a planar electrode identification circuit.

* * * * *